United States Patent

Kampe et al.

[11] 3,968,129
[45] July 6, 1976

[54] AZIDOPHENOL AMINE COMPOUNDS AND THERAPEUTIC COMPOSITIONS

[75] Inventors: Wolfgang Kampe, Heddesheim; Kurt Stach, Mannheim-Waldhof; Max Thiel, Mannheim; Wolfgang Bartsch, Viernheim; Karl Dietmann, Mannheim-Vogelstang, all of Germany

[73] Assignee: Boehringer Mannheim G.m.b.H., Mannheim, Germany

[22] Filed: Jan. 28, 1975

[21] Appl. No.: 544,720

[30] Foreign Application Priority Data

Feb. 22, 1974 Germany............................ 2408522

[52] U.S. Cl................................ 260/349; 424/330
[51] Int. Cl.²........................................ C07C 117/00
[58] Field of Search..................................... 260/349

[56] References Cited
UNITED STATES PATENTS 3,875,232   4/1975   Magee ............................. 260/349

*Primary Examiner*—Lewis Gotts
*Assistant Examiner*—Cary Owens
*Attorney, Agent, or Firm*—Burgess, Dinklage & Sprung

[57] ABSTRACT

New amine derivatives of azidophenols having the formula:

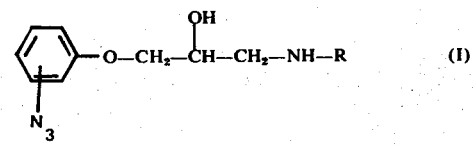

wherein
R is straight-chained or branched alkyl;
and the pharmacologically compatible salts thereof; inhibit adrenogenic β-receptors and are suitable for the treatment and prophylaxis of cardiac and circulatory diseases.

6 Claims, No Drawings

AZIDOPHENOL AMINE COMPOUNDS AND THERAPEUTIC COMPOSITIONS

The present invention is concerned with new azidophenol amine compounds, and to therapeutic compositions and uses thereof.

The new amine derivatives of azidophenols according to the present invention are compounds of the formula:

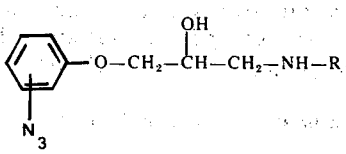
(I)

wherein
R is straight-chained or branched alkyl;
and the pharmacologically compatible salts thereof.

The alkyl radical R is preferably branched and can contain up to 6 and preferably 3 or 4 carbon atoms.

The new compounds (I) and the pharmacologically compatible salts thereof bring about the inhibition of adrenogenic β-receptors and are, therefore, suitable for the treatment and prophylaxis of cardiac and circulatory diseases.

The new compounds (I) according to the present invention, in comparison with the known 1-phenoxy-3-aminopropan-2-ol derivatives, possess surprisingly superior properties.

The new compounds according to the present invention can be prepared, for example, by one of the following methods:

a. reaction of compound of the formula:

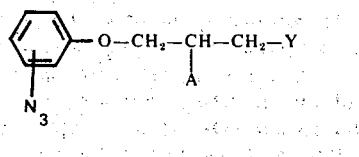
(II)

with a compound of the formula:

Z — R (III), wherein R has the same meaning as above, one of the symbols Y and Z stands for an amino group and the other one for a reactive residue and A is a hydroxyl group or, together with Y, represents an oxygen atom; or b. reaction of a compound of the formula:

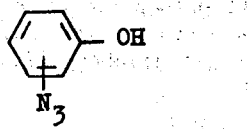
(IV)

with a compound of the formula:

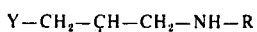
Y—CH₂—CH—CH₂—NH—R (V),
    |
    A wherein A, Y and R have the same meanings as above; whereafter, if desired, the compounds obtained are converted into their pharmacologically compatible salts.

The reactive residues Y and Z in the compounds of formulae (II), (III) and (V) are preferably acid residues, for example of hydrohalic or sulfonic acids.

The reaction of the compounds of formula (II) with compounds of formula (III) according to process a), as well as of compounds of formula (IV) with compounds of formula (V) according to process b), is preferably carried out under reflux conditions in an organic solvent which is inert under the reaction conditions, for example, ethanol, n-butanol, dioxan or dimethyl formamide. The reaction can also be carried out by mixing molar amounts of the reaction components and either leaving the reaction mixture to stand at ambient temperature or by heating.

The reaction of compounds of formula (IV) with compounds of formula (V) according to process b) is preferably carried out with the exclusion of oxygen and in the presence of an acid acceptor. However, it is also possible to use an alkali metal salt of the hydroxy compound of formula (IV).

The invention also concerns the 2-, 3- and 4-(2,3-epoxypropoxy)-azidobenzenes preferably used as starting materials, as well as those embodiments of the process in which there is used a starting material in the form of a crude mixture formed under the reaction conditions or in the form of a salt.

For the conversion of compounds of formula (I) into their pharmacologically compatible salts, they are reacted, preferably in an organic solvent, with an equivalent amount of an inorganic or organic acid, for example, hydrochloric acid, hydrobromic acid, phosphoric acid, sulfuric acid, acetic acid, citric acid or maleic acid.

Preferred compounds according to the present invention, in addition to those mentioned in the following specific Examples, include 4-(2-hydroxy-3-isopropylamino-propoxy)-azidobenzene and 4-(2-hydroxy-3-tert.-butylamino-propoxy)-azidobenzene.

The following Examples are given for the purpose of illustrating, without limiting, the present invention:

EXAMPLE 1

Preparation of 2-(2-Hydroxy-3-isopropylaminopropoxy)-azidobenzene 7.9 g (0.041 mol) 2-(2,3-epoxypropoxy)-azidobenzene were dissolved in 50 ml. isopropylamine and left to stand for 2 days at ambient temperature. For completion of the reaction, the reaction mixture was heated for 2 hours under gentle reflux. The reaction mixture was then carefully evaporated in a vacuum and the residue dissolved in 200 ml. hot ligroin. A small amount of insoluble material was filtered off. The precipitate obtained after cooling was filtered off with suction, dissolved in 50 ml. ethyl acetate and the product precipitated out by the addition of ethereal hydrochloric acid. After filtering off with suction and drying, there was obtained 4.2 g (36% of theory) 2-(2-hydroxy-3-isopropylaminopropoxy)-azidobenzene hydrochloride; m.p. 131°C.

The 2-(2,3-epoxypropoxy)-azidobenzene used as starting material can be prepared in the following manner:

36 g moist sodium salt of azidophenol (obtained from 28.8 g (0.264 mol) 2-aminophenol by the method described by M. O. Forster and H. E. Fierz, J.A.C.S., 91, 1352) were stirred for 4 to 5 hours at 50°C. with 100 ml. epichlorohydrin. Thereafter, excess epichlorohydrin was distilled off and the residue was mixed with ether and water. The ethereal phase was washed several times with water, dried over anhydrous sodium sulfate and evaporated. There were obtained 18 g (36% of theory, referred to 2-aminophenol) of chromatographically almost pure 2-(2,3-epoxypropoxy)-azidobenzene in the form of a yellowish oil which could not be crystallized.

EXAMPLE 2

Preparation of 2-(2-Hydroxy-3-tert.-butylaminopropoxy)-azidobenzene

In a manner analogous to that described in Example 1, from 20.0 g (0.105 mol) 2-(2,3-epoxypropoxy)-azidobenzene and 50 ml. tert.-butylamine, there were obtained 13.2 g (33% of theory) 2-(2-hydroxy-3-tert.-butylaminopropoxy)-azidobenzene maleate; m.p. 117° – 119°C.

EXAMPLE 3

Preparation of 3-(2-Hydroxy-3-isopropylaminopropoxy)-azidobenzene 8.8 g (0.046 mol) 3-(2,3-epoxypropoxy)-azidobenzene were left to stand for 2 days at ambient temperature in 50 ml. isopropylamine and thereafter gently boiled for 2 hours. The reaction mixture was evaporated in a vacuum and the residue mixed with 1N acetic acid and ether. The ethereal phase was discarded. The acetic acid phase was rendered weakly alkaline with solid sodium bicarbonate and extracted with ether several times. The ethereal phase was dried, clarified with active charcoal and evaporated. The crystalline residue (7.3 g) which crystallized out upon trituration with ligroin was taken up in ethyl acetate and the solution mixed with the calculated amount of maleic acid (dissolved in a little isopropanol). After suction, filtration and drying of the precipitate thereby obtained, there were obtained 7.2 g (43% of theory) 3-(2-hydroxy-3-isopropylaminopropoxy)-azidobenzene maleate; m.p. 104° – 105°C.

The 3-(2,3-epoxypropoxy)-azidobenzene used as starting material was obtained, analogously to Example 1, from the sodium salt of 3-azidophenol and epichlorohydrin in the form of a pale yellow oil which could not be crystallized. The yield was 34% of theory, referred to the 3-aminophenol.

EXAMPLE 4

Preparation of 3-(2-Hydroxy-3-tert.-butylaminopropoxy)azidobenzene

In a manner analogous to that described in Example 3, from 8.8 g (0.046 mol) 3-(2,3-epoxypropoxy)-azidobenzene and 50 ml. tert.-butylamine, there were obtained 7.3 g (about 42% of theory) 3-(2-hydroxy-3-tert.-butylaminopropoxy)-azidobenzene maleate; m.p. 128°C.

The following tests were carried out to determine the cardiac $\beta$-receptor blocking activity and the acute toxicity of certain compounds representative of the invention, as well as of a conventional comparison compound.

The test compounds were as follows:

Compound 1   2-(2-Hydroxy-3-isopropylaminopropoxy)-azidobenzene
Compound 2   3-(2-Hydroxy-3-isopropylaminopropoxy)-azidobenzene
Compound 3   3-(2-Hydroxy-3-tert.-butylaminopropoxy)-azidobenzene
Compound 4   2-(2-Hydroxy-3-tert.-butylaminopropoxy)-azidobenzene
Comparison   "Practolol"
Compound A   (4-[2-hydroxy-3-isopropylaminopropoxy]acetanilide)

The cardiac $\beta$-receptor blocking activity of the test compounds was evaluated by determination of the inhibition of isoprenalin-induced heart frequency increase in wake rabbits. This type of inhibition is a typical property of $\beta$-receptor blocking bio catalysts.

The tests were carried out on rabbits weighing between 2 to 3.5 kg settled in wooden cages with EKG-electrodes inserted into the hind-quarters s.c. The heart frequency was read via an integrator (15 seconds) as a digital value. The substances to be tested were infused through a small tube to the ear vein of the rabbits over a period of 15 minutes 30 minutes after completion of the infusion, isoprenalin (1 $\mu$g/kg) was intravenously injected. The results were set forth in terms of the reduction of the heartbeat increase induced by isoprenalin and a value ($DE_{250}$) calculated as the dosage required to limit such increase to 250 heart beats/min.

In another series of tests, the acute toxicity in mice of the test compounds by intravenous administration was determined as a measure of the tolerance (calculated as $LD_{50}$ = dosage at which 50% of the mice die). The substances were injected, within a time period of 5 seconds, in dissolved form into the tail vein of 5 male and 5 female mice each, in increasing dosages. From the results (percentage of dead animals) at the various dosages, the mean lethal dosage was ascertained graphically or by way of programmed test analysis.

The results of both series of tests are set forth in the table below which contains, in addition, a calculated value expressing the ratio of $LD_{50}$ : $DE_{250}$ for each test compound.

TABLE

| Test Substance | Acute Toxicity $LD_{50}$ Mouse mg/kg i.v. | Blocking of Isoprenalin Tachycardia in wake rabbits | | $DE_{250}=$ mg/kg i.v. | $\dfrac{LD_{50}}{DE_{250}}$ |
| --- | --- | --- | --- | --- | --- |
| | | Dosage mg/kg i.v. | Heartbeat Frequency $\bar{x}\pm s_{\bar{x}}$ (Beats/minute) | | |
| Control | — | without Isoprenalin | 205± 9 | — | — |

TABLE-continued

| Test Substance | Acute Toxicity LD$_{50}$ Mouse mg/kg i.v. | Blocking of Isoprenalin Tachycardia in wake rabbits | | DE$_{250=}$ mg/kg i.v. | $\frac{LD_{50}}{DE_{250}}$ |
| --- | --- | --- | --- | --- | --- |
| | | Dosage mg/kg i.v. | Heartbeat Frequency $\bar{x}\pm s_{\bar{x}}$ (Beats/minute) | | |
| Control | — | with Isoprenalin | 338±10 | — | — |
| Comparison Compound A | 69 | 0.5 | 307± 7 | 2.5 | 28 |
| | | 1.0 | 264± 9 | | |
| | | 2.0 | 250± 4 | | |
| | | 5.0 | 246± 7 | | |
| | | 10.0 | 217± 4 | | |
| | | 20.0 | 225± 6 | | |
| Compound 1 | 25 | 0.01 | 288± 8 | 0.3 | 80 |
| | | 0.1 | 252±10 | | |
| | | 0.5 | 250± 5 | | |
| | | 1.0 | 236±11 | | |
| | | 5.0 | 223± 6 | | |
| Compound 2 | 50 | 0.5 | 282± 9 | 1.3 | 40 |
| | | 1.0 | 258±10 | | |
| | | 5.0 | 205± 9 | | |
| Compound 3 | 50 | 0.1 | 317±10 | 0.8 | 60 |
| | | 0.5 | 256±10 | | |
| | | 10 | 244± 8 | | |
| | | 2.0 | 222± 6 | | |
| | | 5.0 | 235±10 | | |
| Compound 4 | 29 | 0.1 | 282± 5 | 0.5 | 58 |
| | | 0.5 | 237± 7 | | |
| | | 1.0 | 246± 6 | | |
| | | 5.0 | 245±14 | | |

*Interpolated dosage which limits the frequency increase to 250 beats/min.

The above data show that the inventive compounds are effective as tachycardia blockers at dosages 2 to 8 times smaller than that required of the comparison compound "Practolol" to give the same effect.

Also, it will be seen that inventive compounds provide a far greater margin of safety in that the margin between the dosage which is toxic to mice, and the dosage giving tachycardia blocking, is very large and substantially larger than the margin provided by the comparison compound.

The compounds according to the present invention are thus unexpectedly superior in effectiveness to known compounds and thus present a valuable contribution to the art.

The dosage of the novel compounds of the present invention depends on the age, weight, and condition of the patient being treated. Generally speaking, for aduloral administration, the preferred unit dosage of active compound with a suitable pharmaceutical diluent or lubricant is 1 mg. – 40 mg. four times a day. In general the oral dosage is 20 – 40 mg., whereas the intravenous dosage is generally 1 – 5 mg., four times a day.

For the preparation of pharmaceutical compositions, at least one of the new compounds according to the present invention is mixed with appropriate solid or liquid pharmaceutical diluents or carriers and, if desired, also with odoriferous, flavoring and coloring material and then formed into, for example, tablets or dragees or, with the addition of appropriate adjuvants, suspended or dissolved in water or oil, for example in olive oil.

The new compounds according to the present invention of general formula (I) and the salts thereof can be administered enterally or parentally in solid or liquid form. As injection medium, it is preferred to use water which contains the conventional additives for injection solutions, for example, stabilizing agents, solubilizing agents or buffers. Additives of this kind include, for example, tartrate and citrate buffers, ethanol, complex-forming agents (such as ethylenediamine-tetraacetic acid and the non-toxic salts thereof), and high molecular weight polymers (such as polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agaragar, calcium phosphate, magnesium stearate, animal and vegetable fats and solid high molecular weight polymers (such as polyethylene glycols); compositions which are suitable for oral administration can, if desired, contain flavoring and sweetening agents.

For preparing compounds such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral adminstration.

It will be appreciated that the instant specification and examples are set forth by way if illustration and not limitation, and that various modificatons and changes may be made without departing from the spirit and scope of the present invention.

What is claimed is:

1. Azidophenol amine compound of the formula:

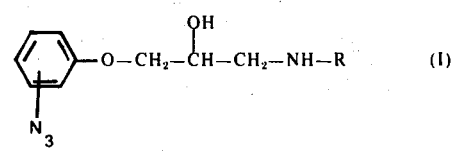

(I)

wherein

R is straight-chained or branched alkyl of up to 6 carbon atoms; and the pharmacologically acceptable salts thereof.

2. Azidophenol amine compound as claimed in claim 1, wherein R is branched alkyl and contains up to 6 carbon atoms.

3. Azidophenol amine compound as claimed in claim 1, designated 2-(2-Hydroxy-3-isopropylaminopropoxy)-azidobenzene.

4. Azidophenol amine compound as claimed in claim 1, designated 3-(2-Hydroxy-3-isopropylaminopropoxy)-azidobenzene.

5. Azidophenol amine compound as claimed in claim 1, designated 3-(2-Hydroxy-3-tert.-butylaminopropoxy)-azidobenzene.

6. Azidophenol amine compound as claimed in claim 1, designated 2-(2-Hydroxy-3-tert.-butylaminopropoxy)-azidobenzene.

* * * * *